US005728728A

United States Patent [19]
Kozachuk

[11] Patent Number: 5,728,728
[45] Date of Patent: Mar. 17, 1998

[54] METHODS OF PROVIDING NEUROPROTECTION

[76] Inventor: Walter E. Kozachuk, 8484 16th St. #702, Silver Spring, Md. 20910

[21] Appl. No.: 632,338

[22] Filed: Apr. 10, 1996

[51] Int. Cl.[6] .......................... A61K 31/27; C07C 271/10
[52] U.S. Cl. .............................................. 514/483; 560/158
[58] Field of Search .................................. 514/534, 541, 514/483; 560/158

[56] References Cited

U.S. PATENT DOCUMENTS

| | | | |
|---|---|---|---|
| 4,978,680 | 12/1990 | Sofia | 514/534 |
| 5,292,772 | 3/1994 | Sofia | 514/534 |
| 5,492,930 | 2/1996 | Coffin | 514/478 |

OTHER PUBLICATIONS

Amaee, F. R. et al., NG-methyl-L-arginine protects the guinea pig Cochlea from the Cytotoxic effects of Pneumolyfin, Acta OTO-Laryngolo-Gica, vol. 115 (3), pp. 386-391, 1995.

Hayes, M.P. et al, Brain (1993), 116, 1425-1450, "A mechanism of quinolinic acid formation by brain in inflammatory neurological disease".

Cascella, N.G. et al, J. Neural Transm [GenSect] (1994) 95:105-111, "d-Cycloserine adjuvant therapy to conventional neuroleptic treatment in schizophrenia: an open-label study".

Serra, M. et al, European Journal of Pharmacology 265 (1994) 185-188, "Felbamate antagonizes isoniazid- anti FG 7142-induced reduction of $GABA_A$ receptor function in mouse brain".

Fletcher, E.J. et al, European Journal of Pharmacoloqy, 235 (1993) 291-295, "Haloperidol interacts with the strychnine-insensitive glycine site at the NMDA receptor in cultured mouse hippocampal neurones".

White, H.S. et al, Epilepsy Research 20 (1995) 41-48, "Felbamate modulates the strychnine-insensitive glycine receptor".

Melis, M.R. et al, Neuroscience Letters 179 (1994) 9-12, "Nitric oxide synthase inhibitors prevent N-methyl-D-aspartic acid-induced penile erection and yawning in male rats".

Hayashi, T., Department of Physiology, School of Medicine, Keio University, (Received for publication Jul. 10, 1952), "A Physiological Study of Epileptic Seizures Following Cortical Stimulation in Animals and Its Application To Human Clinics".

Baxter, M.G. et al. Neurobiology of Aging, vol. 15, No. 2, pp. 207-213, 1994, "D-Cycloserine, a Novel Cognitive Enhancer, Improves Spatial Memory in Aged Rats".

Carlson, M.D. et al, Neurobiology of Aging, vol. 14, pp. 343-352, 1993, "NMDA, AMPA and Benzodiazepine Binding Site Changes in Alzheimer's Disease Visual Cortex".

Carter, A.J., Drugs of the Future, 1992, 17(7): 595-613, "Glycine antagonists: Regulation of the NMDA receptor-channel complex by the strychnine-insensitive glycine site".

Cheshire, W.P., The Clinical Journal of Pain, vol. 11, No. 2, 139-142 (1995) "Felbamate Relieved Trigeminal Neuralgia".

Chronopoulos, A. et al, Epilepsia, 34(2):359-366, 1993, "Neuroprotective Effect of Felbamate After Kainic Acid-Induced Status Epilepticus".

Coffin, V. et al, European Journal of Pharmacology, 256 (1994) R9-R10, "Selective antagonism of the anticonvulsant effects of felbamate by glycine".

Corbett, R. et al, Drug Development Research 24:201-205 (1991), "Effects of HA-966 on Conflict, Social Interaction, and Plus Maze Behaviors".

Cornford, E.M. et al, Epilepsia, 37(1):15-18, 1996, "Distribution of Felbamate in Brain".

Cotman, C.W. et al, Ann. Rev. Neurosci. 1988 11:61-80, "Excitatory Amino Acid Neurotransmission: NMDA Receptors and Hebb-Type Synaptic Plasticity".

Croucher, M.J. et al, Brain Research, 543 (1991) 91-96, "The influence of strychnine-insensitive glycine receptor agonists and antagonists on generalized seizure thresholds".

Croucher, M .J. et al, Neuroscience Letters, 118 (1990) 29-32, "7-Chlorokynurenic acid, a strychnine-insensitive glycine receptor antagonist, inhibits limbic seizure kindling".

During, M.J. et al, The Lancet, vol 341, Jun. 26, 1993, 1607-1610, "Extracellular hippocampal glutamate and spontaneous seizure in the conscious human brain".

De Sarro, Giovambattista et al, European Journal of Pharmacology 262 (1944) 11-19, "Excitatory amino acid neurotransmission through both NMDA and non-NMDA receptors is involved in the anticonvulsant activity of felbamate in DBA2 mice".

Fink, K. et al, Naunyn-Schmiedeberg's Arch Pharmacol (1995) 352:394-401, "Stimulation of serotonin release in the rat brain cortex by activation of ionotropic glutamate receptors and its modulation via $\alpha_2$-heteroreceptors".

Finkelstein, J.E. et al, Pharmacoloqy Biochemistry and Behavior, vol. 49, No. 3, pp. 707-710, 1994, "Milacemide Treatment in Mice Enhances Acquisition of a Morris-Type Water Maze Task".

Fisher, M. et al, Stroke, vol. 25, No. 5, May 1994 "Prophylactic Neuroprotection for Cerebral Ischemia".

Fishkin, R.J. et al, Behavioral and Neural Biology, 59, 150-157 (1993), "D-Cycloserine Attenuates Scopolamine-Induced Learning and Memory Deficits in Rats".

Heyes, M.P. et al, Journal of the Neurological Sciences 133 (1995) 112-118, "Quinolinic acid in tumors, hemorrhage and bacterial infections of the central nervous system in children".

(List continued on next page.)

Primary Examiner—C Warren Ivy
Assistant Examiner—Charanjit S. Aulakh
Attorney, Agent, or Firm—Myers Liniak & Berenato

[57] ABSTRACT

Novel methods are disclosed for treating acute and chronic neurological disease and attenuating further neuronal cell death in neurological diseases, employing a glycine site antagonist at the NMDA (N-methyl-D-aspartate) complex, e.g., 2-phenyl-1,3-propanediol dicarbamate (felbamate).

6 Claims, No Drawings

OTHER PUBLICATIONS

Hill, R.R. et al, *Psychosomatics*, pp. 404–406, "Secondary Mania Associated With the Use of Felbamate".

Hutson, P.H, et al, Merck Sharp and Dohme Research Laboratories, Neuroscience Research Centre, Terlings Park, Eastwick Road, Harlow, Essex, CM20 2QR, pp. 2037–2044, "R–(+)–HA–966, a glycine/NMDA receptor antagonist, selectively blocks the activation of the mesolimbic dopamine system by amphetamine".

Imamura, Y. et al, *The Journal of Pharmacology and Experimental Therapeutics*, vol. 275, No. 1, pp. 177–182, "Felbamate Relieves Several Abnormal Pain Sensations in Rats with an Experimental Peripheral Neuropathy".

Kemp, J .A. et al, 1993, *Elsevier Science Publishers Ltd (UK)*, TIPS–Jan. 1993 [vol. 14], "The glycine site of the N MDA receptor–five years on".

Kerrick, M. et al, *Neurology* 45, Jan. 1995, pp. 185–187, "Involuntary movement disorders associated with felbamate".

J. Clin Psychopharmacol, vol. 15/No. 4, Aug. 1995, pp. 292–293, "Psychosis Associates with Felbamate Treatment".

Harmsworth, W.L. et al, *Epilepsia*, vol. 34, Suppl. 2, 1993, pp. 92–93, "Felbamate Modulates Glycine Receptor Function".

Kretschmer, Beate D., *Neuroscience Letters* 179 (1994) 115–118, "Felbamate, an anti–convulsive drug, has anti–partinsonian potential in rats".

Leeson, P.D. et al, *Journal of Medicinal Chemistry*, vol. 37, No. 24,. Nov. 25, 1994, "The Glycine Site on the NMDA Recpetor:Structure–Activity Relationships and Therapeutic Potential".

Lipton, S.A. et al, *Mechanisms of Disease–Lipton and Rosenberg*, vol. 330, No. 9, pp. 613–622, "Excitatory Amino Acids As A Final Common Pathway For Neurologic Disorders".

McBain, C.J. et al, *Physiological Reviews*, vol. 74, No. 3, Jul. 1994, pp. 723–760, "N–Methyl–D–Aspartic Acid Receptor Structure and Function".

McCabe, R.T. et al, *The Journal of Pharmacology and Experimental Therapeutics*, vol. 264, No. 3, pp. 1248–1252, "Evidence for Anticonvulsant and Neuroprotectant Action of Felbamate Mediated by Strychnine–Insensitive Glycine Receptors".

Mellick, Gary A., DO, *Journal of Pain and Symptom Management*, vol. 10, No. 5, Jul. 1995, pp. 392–395, "Hemifacial Spasm: Successful Treatment with Felbamate".

Millian, M.J. et al, *Neuroscience Letters* 178 (1994) 139–143, "Chemically–diverse ligands at the glycine B site coupled to N–methyl–D–Oaspartate (NMDA) receptors selectively block the late phase of formalin–induced pain in mice".

Miyoshi, R. et al, *Synapse* 6:338–343 (1990), "Age–Related Changes of Strychnine–insensitive Glycine Receptors in Rat Brain" as Studies by In Vitro Autoradiography.

Monaghan, D.T. et al, *Annu. Rev. Pharmacol. Toxicol,* 1989, 29:365–402, "The Excitatory Amino Acid Receptors: Their Classes, Pharmacology, and Distinct Properties in the Function of the Central Nervous System".

Ney, G.C. et al, *Neurology*, May 1994, pp. 980–981, "Thrombocytopenia in association with adjunctive felbamate use".

Olney, J.W. et al, *Arch Gen Psychiatry*, vol. 52 Dec. 1995, pp.998–1007, "Glutamate Receptor Dysfunction and Schizophrenia".

O'Neil, M.G. et al, Letters, *The Annals of Pharmacotherapy*, 1995 Apr., vol. 29, p.430, "Felbamate–induced delayed anaphylaxis".

Pennell, P.B., et al, *Neurology*, Mar. 1995, 45:456–460, "Aplastic anemia in a patient receiving felbamate for complex partial seizures".

Priestley, T., et al, *Brain Research*, 531 (1990) 183–188, "The effect of NMDA receptor glycine site antagonists on hypoxia–induced neurodegeneration of rat cortical cell cultures".

Reynolds, G.P., et al, *Journal of the Neurological Sciences*, 125 (1994) 46–49, pp.46–49. "Deficit of [$^3$H]L–689,560 binding to the glycine site of the glutamate/NMDA receptor in the brain in Huntington's disease".

Rho, J.M., et al, *Annals of Neurology*, vol. 35, No. 2, Feb. 1994, pp. 229–234, "Mechanism of Action of the Anticonvulsant Felbamate:Opposing Effects on N–Methyl–D–Aspartate and y–Aminobutyric Acid$_A$ Receptors".

Rothstein, J.D., et al, *Annals of Neurology*, vol. 28, No. 1, Jul. 1990, pp. 18–25, "Abnormal Excitatory Amino Acid Metabolism in Amyotrophic Lateral Sclerosis".

Schulte, S., et al, *Neuro Toxicology*, 16(2):309–318, 1995, "In Vitro and In Vivo Effects of Lead on Specific $^3$H–MK–801 Binding to NMDA–Receptors in the Brain of Mice".

Shaw, P.J., et al, *Brain Research*, 637 (1994) 297–302, "N–Methyl–D–aspartate (NMDA) receptors in the spinal cord and motor cortex in motor neuron disease: a quantitative autoradiographic study using [$^3$H]MK–801".

Singh, L., et al, *European Journal of Pharmacology*, 186 (1990) 129–132, "The discriminative stimulus properties of (+)–HA–966, an antagonist at the glycine/N–methyl–D–aspartate receptor".

Sofia, R. Duane, Letters, Copyright© 1994 by the American Neurological Association, p. 677, "Mechanism of Action of the Anticonvulsant Felbamate: Opposing Effects on N–Methyl–D–Aspartate and y–Aminobutyric Acid$_A$ Receptors".

Subramaniam, S., et al, *The Journal of Pharmacology and Experimental Therapeutics*, vol. 273, No. 2, pp. 878–886, "Felbamate Block the N–Methyl–D–Aspartate Receptor".

Taylor, L.A., et al, *European Journal of Pharmacology–Molecular Pharmacology Section*, 289 (1995) 229–233, "Felbamate, a novel antiepileptic drug, reverses N–methyl–D–aspartate/glycine–stimulated increases in intracellular $Ca^{2+}$concentration".

Ticku, M. K., et al, *Epilepsia,* vol. 32, No. 3, 1991, "Effect of Anticonvulsant Felbamate on GABA$_A$ Receptor System".

Travaglini, M.T., *Pharmacotherapy,* vol. 15, No. 2, 1995, pp. 260–264, "Tosic Epidermal Necrolysis After Initiation of Felbamate Therapy".

Edwards, K.R., *Neurology,* 45, Oct. 1995, p. 1951, "Felbamate and tremor".

Tsuchida, E., et al, *Journal of Neurotrauma,* vol. 12, No. 3, 1995, pp. 279–288, "The Effect of the Glycine Site–specific N–Methyl–D–Aspartate Antagonist ACEA1021 on Ischemic Brain Damage Caused by Acute Subdural Hematoma in the Rat".

Vaccarino, A.L., et al, *Brain Research,* 615 (1993) 331–334, "NMDA receptor antagonists, MK–801 and ACEA–1011, prevent the development of tonic pain following subcutaneous formalin".

Van Harmveld, A., *Journal of Neurochemistry*, 1959, vol. 3, pp. 300–315, "Compounds in Brain Extracts Causing Spreading Depression of Cerebral Cortical Activity and Contraction of Crustacean Muscle".

Virgo, L., et al, *Brain Research*, 676 (1995) 196–204, "Induction of the immediate early gene c–jun in human spinal cord in amyotrophic lateral sclerosis with concomitant loss of NMDA receptor NR–1 and glycine transporter mRNA".

Wallis, R.A., et al, *Neuropharmacology and Neurotoxicology*, vol. 4, No. 7, Jul. 1993, "Glycine reversal of felbamate hypoxic protection".

Wallis, R.A., et al, *Brain Research*, 685 (1995) 225–235, "Glycine–induced CA1 excitotoxicity in the rat hippocampal slice".

Wamsley, J.K., et al, *Experimental Neurology*, 129,244–250 (1994), "Interaction of Felbamate with [$^3$H]DCKA–Labeled Strychnine–Insensitive Glycine Receptors in Human Postmortem Brain".

Wasterlain, C.G., et al, *Neurology*, 1993;43:2303–2310, "Posthypoxic treatment with felbamatge is neuroprotective in a rat model of hypoxia–ischemia".

Watkins, J.C., et al, *Ann. Rev. Pharmacol. Toxicol.*, 1981, 21:165–204, "Excitatory Amino Acid Transmitters".

Watkins, J.C., et al, *Elsevier Science Publishers Ltd (UK)*, TIPS–Jan. 1990 [vol. 11], pp. 25–33, "Structure–activity relationships in the develoment of escitatory amino acid receptor agonists and competitive antagonists".

White, H.S., et al, *Epilepsia*, vol. 33, No. 3, 1992, "A Neuropharmacological Evaluation of Felbamate as a Novel Anticonvulsant".

Widdowson, P.S., et al, *Journal of Neurochemistry*, vol. 64, No. 2, 1995, "NMDA Receptors in Rat Cerebellum and Forebrain: Subtle Differences in Pharmacology and Modulation".

Wilensky, A.J., et al, *Epilepsia*, vol. 26, No. 6, 1985, "Pharmacokinetics of W–554 (ADD 03055) in Epileptic Patients".

Wlaz, P., et al, *European Journal of Neuroscience*, vol. 6, pp. 1710–1719, 1994, "Low Doses of the Glycine/NMDA Receptor Antagonist (+)–HA–966 but not D–Cycloserine Induce Paroxysmal Activity in Limbic Brain Regions of Kindled Rats".

METHODS OF PROVIDING NEUROPROTECTION

FIELD OF THE INVENTION

The present invention relates to pharmaceutical compositions which are antagonists at the glycine site on NMDA (N-methyl-D-aspartate) receptor complex, and to methods for the attenuation of acute or chronic neuronal damage in neurological disease ("neuroprotection").

BACKGROUND OF THE INVENTION

The major excitatory neurotransmitter in the central nervous system is L-glutamate. The amino acids glutmate and aspartate cause convulsive activity when applied to the cerebral cortex (Hayashi, T., Jpn. J. Physiol., 3:46–64, 1952). Classification of the excitatory receptors include the AMPA, kainate and NMDA receptors (Watkins, J. C. Ann. Rev. Pharmacol. Toxicol., 21:165–204, 1989).

Unique features of the NMDA receptor-channel complex include: a sensitivity to blockade by physiological concentrations of $Mg^{++}$, a high permeability to $Ca^{++}$, and a requirement for coactivation by glycine. Thus, glycine and glutamate binding sites are allosterically coupled at the NMDA receptor complex. (Kemp, J. A., Trends Pharmacol Sci., 14(1):20–5, 1993).

Excitatory amino acid receptors are divided into NMDA and non-NMDA (kainate and AMPA) subtypes (Monaghan, D. T., Annu. Rev. Pharmacol. Toxicol., 29, 365–402 1989). The NMDA receptor complex is located on the neuronal cell surface and is comprised of multiple (i.e., glycine, polyamine, NMDA) binding sites as well as an ion-channel which has several internal binding sites. NMDA receptors are widely distributed in brain and spinal cord, with the highest densities in cerebral cortex and hippocampus (McBain, C. J., Physiol. Rev., 74:723–760, 1994, Leeson, P. D., J. Med. Chem., 37(24):4053–4067, 1994). The NMDA receptor has an important function in longterm potentiation (LTP) which is critical for the process of learning and memory (Cotman, C. W., Annu. Rev. Neurosci., 11:61–80, 1988).

The major excitatory neurotransmitter in the central nervous system is L-glutamate. Glutmate is the principal excitatory neurotransmitter in the brain and has an integral role in neurologic function including cognition, memory, movement and sensation. A recent review of neurological diseases has implicated a role for glutmate in the pathogenesis of multiple acute and chronic neurological disorders (Lipton, S. A., NEJM 330(9):613–622, 1994). In both NMDA and non-NMDA classes of receptors, glutmate opens an ion channel which leads to a rapid influx of intracellular cations ($Na^+$ and $Ca^{++}$). Unique features of the NMDA receptor-channel complex include a strychnine insensitivity, blockade by physiological concentrations of $Mg^{++}$, a high permeability to $Ca^{++}$, and a requirement for coactivation by glycine. Thus, glycine and glutmate binding sites are allosterically coupled at the NMDA receptor complex, and glycine is required for activation of this receptor (Carter, A. J., Drugs Fur., 17(7):595–613, 1992, Leeson, P. D., J. Med. Chem, 37(24):4053–4067, 1994).

The amino acid glutmate causes convulsive activity (Hayashi, T., Jpn. J. Physiol., 3:46–64, 1952), produces cortical spreading depression (Van Harreveld, A., J. Neurochem., 3:300–315, 1959) and is elevated prior to complex partial seizures (During, M. J., Lancet., 341:1607–1610, 1993). Intracerebral administration of a glycine agonist has been shown to increase the potency of NMDA in inducing seizures in mice (Singh, L., Eur. J. Pharmacol., 186:129–132, 1990).

Functional glycine antagonists can have either high intrinsic activity (D-cycloserine) or low intrinsic activity (HA-966). The compound HA-966 also displays weak partial agonist effects at the glycine site, bears the risk of proconvulsant activity. (Wlaz, P., Eur. J. Neurosci, 6(11):1710–17819, 1994)

Felbamate (2-phenyl-1,3-propanediol dicarbamate) is a known pharmaceutical compound having been described in U.S. Pat. Nos. 2,884,444 (1959). Felbamate is a glycine site antagonist at the NMDA receptor.

U.S. Pat. No. 4,978,680 relates to the use of felbamate for the prevention and control of epileptic seizures. U.S. Pat. No. 5,082,861 relates to the use of felbamate for the prevention and control of epileptic seizures associated with complex partial seizures. U.S. Pat. No. 5,292,772 relates to the use of felbamate for the prevention and control of epileptic seizures associated with Lennox-Gastaut syndrome. U.S. Pat. No. 4,868,327 discloses a synthesis of felbamate.

Felbamate is a modulator of NMDA receptor function, and a glycine site antagonist (McCabe, R. T., J. Pharmacol. Exp. The., 264(3):1248–1252, 1993, Sofia, 1994, Wamsley, J. K., Exp. Neurol., 129(2):244–250, 1994, Taylor, L. A., Eur. J. Pharmacol., 289(2):229–233, 1995, White, H. S., Epilepsy Res., 20(1):41–48, 1995) but also has other reported mechanisms of actions (White, H. S., Epilepsia, 33(3):564–572, 1992, De Sarro, G., Eur. J. Pharmacol, 262(1–2):11–19, 1994, Serra, M., Eur. J. Pharmacol, 265 (3):185–188, 1994, Rho, J. M., Ann. Neurol., 25:229–234, 1994, Subramanian, S., J. Pharmacol. Exp. The., 273:878–886, 1995). Felbamate does not cause the transient neuropathological changes seen in brain neurons after competitive antagonist administration (Olney, J. W., Arch. Gen. Psych., 52:998–1007, 1995).

Felbamate is protective against NMDA-induced convulsions in mice (White, H. S., Epilepsia 33(3):564–572, 1992; Sofia, Ann. Neurol., 36(4):677–678, 1994). 2-phenyl-1,3-propanediol dicarbamate showed efficacy in controlling partial seizures in epileptic patients (Wilensky, A. J., Epilepsia, 26(6); 602–606, 1985). The major anticonvulsant action of felbamate is due to interaction at the strychnine-insensitive glycine site at the NMDA complex (McCabe, R. T., J. Pharmacol. Exp. The., 264(3):1248–1252, 1993; White, H. S., Epilepsy Res., 20(1):41–48, 1995). In the rat hippocampal slice model of neural injury, felbamate provided excellent protection from glycine-induced injury, while 7-Cl-kynurenic acid (another glycine site antagonist) appeared to be toxic (Wallis, R. A., Brain Res., 685(1–2):115–125, 1995).

Felbamate has also been reported to interact at the AMPA/ kainate receptor (De Sarro, G., Eur. J. Pharmacol., 262 (1–2): 11–19, 1994), facilitate the function of the GABA receptor (Serra, M., Eur. J. Pharmacol., 265(3): 185–188, 1994, Rho, J. M., Ann. Neurol., 25:229–234, 1994), and modulate $Na^+$ channel conductance (White, H. S., Epilepsia, 33(3):564–572, 1992). Felbamate decreased delayed neuronal cell death after kainic acid induced status epilepticus in animals (Chronopoulus, A., Epilepsia, 34(2):359–366, 1993). Glycine or d-serine were able to functionally reverse the anticonvulsant (Harmsworth, W. L., Epilepsia, 34(Suppl 2):92, 1993, Coffin, V., Eur. J. Pharmacol., 256:9–10, 1994) and isehemic protective effect (Wallis, R. A., Neuro. Report., 4:951–954, 1993) of felbamate. Conversely, other studies have not confirmed modulation of the GABA receptor (Ticku, M. K., *Epilepsia*, 32(3): 389–391, 1995) or glycine site antagonist mechanism of action (Rho, J. M., *Ann. Neurol.*, 25:229–234, 1994, Subramanian, S., *J. Pharmacol. Exp. The.*, 273:878–886, 1995).

In culture, antagonism of the glycine site or channel of the NMDA receptor prevents hypoxia-induced degeneration (Priestly, T., *Brain Res.*, 531:183–8, 1990). In animal models of stroke (ischemia), felbamate was found to decrease neuronal death and delayed-ischemic necrosis when administered post-hoc (Wastetim, C. G., *Neurology*, 43:2303–2310, 1993). Felbamate has been proposed as a therapeutic treatment for the prophylaxis of stroke in humans (Fisher et al, *Stroke*, 25(5): 1994).

Felbamate and Adverse Events

In clinical studies prior to FDA approval, felbamate was evaluated both as an "add-on" therapy in patients with intractable seizures i.e., in combination with other standard anti-epileptic drugs; and as monotherapy. There were several case reports of a decrease in platelets and other hematologic parameters but these were mild, reversible and occurred in combination with other antiepileptic drugs (i.e., valproic acid, carbamezepine) known to have these side effects. There were no reported cases of liver failure of bone marrow suppression prior to drug approval. The drug interaction of felbamate causes increases in the serum levels of dilantin, valproic acid, phenobarbitol, and the toxic epoxide metabolite of carbamezepine.

Felbamate was approved for use by the FDA in July 1993. In 1994 there were reports of felbamate causing aplastic anemia (Pennel, P. P., *Neurology*, 45:456–460, 1995) in 21 patients with 7 deaths, and hepatic failure in 11 patients with 4 deaths. As a result, the FDA and the manufacturer sent a letter to all physicians in August 1994 requiring the withdrawal of felbamate from patients except in those cases in which the risk of seizure exceeded the risk of aplastic anemia. Warnings were added to the prescribing information and a blood test was required every two weeks.

Other reported adverse events include thromocytopenia (Ney, G. C., *Neurology*, 44:980–981, 1994), toxic epidermal necrolysis (Travagline, M. T., *Pharmacotherapy*, 15(2):260–4, 1995) anaphylaxis (O'Neil, M. G., *Ann. Pharmacother.*, 29(4):430,1995) mania (Hill, R. R., *Psychosomatics*, 36(4):404–6, 1995) psychosis (Knable, M. B., *J. Clin. Psychopharmacol.*, 15(4):292–3, 1995) and movement disorder (Kerrick, J. M., *Neurology*, 45(1):185–7 1995).

OBJECTS OF THE INVENTION

One of the objects of the present invention is to provide compositions and methods for the treatment of acute and chronic neurological disorders that involve excessive activation of the NMDA receptor.

Another object of the present invention is to provide compositions and methods effective to control or attenuate acute or chronic neurological disorders.

A further objective of the present invention is to provide compositions and methods for the prevention and control of acute or chronic neurological disorders that involve excessive activation of the NMDA receptor, which compositions are relatively non-toxic, have a high degree of effectiveness and continue to produce a therapeutic response over long periods of time.

A further object of the invention is to provide a method to visualize and quantitate NMDA receptors in vivo in normal human controls, asymptomatic and clinical disease states.

Still another object of the present invention is to provide a method for the attenuation of neuronal death caused by excessive activation of the NMDA receptor by seizures or status epilepticus.

Moreover, it is a further object of the present invention to provide methods for the attenuation and control of acute and chronic neurological disorders that involve excessive activation of the NMDA receptor.

SUMMARY OF THE INVENTION

The subject invention relates to methods for treating acute and chronic neurological diseases and preventing neuronal cell death in neurological diseases, in mammals including humans, employing a glycine site antagonist at the NMDA receptor. The antagonists are administered intravenously or orally, acutely or chronically to attenuate further neuronal damage and death. Advantageously, the drug is given chronically when the patient has asymptomatic or preclinical neurological disease.

The invention also relates to a method of determining NMDA receptor level in a mammal comprising administering labeled felbamate, and determining the amount of labeled felbamate which is bound to neurons.

DETAILED DESCRIPTION OF THE INVENTION

The present invention relates to pharmaceutical compositions and to methods for the attenuation of acute and chronic neurological disorders that involve excessive activation of the NMDA receptor. Advantageously, the present invention relates to methods for neuroprotection in neurological disease(s) through the administration of therapeutic compositions, either intravenously or orally, which contain for example, as an active ingredient 2-phenyl-1,3-propanediol dicarbamate, commonly known as felbamate. This compound has multiple mechanisms of action, of which one is a glycine site antagonist at the NMDA (N-methyl-D-aspartate) receptor.

NMDA receptor antagonists can be divided into noncompetitive (acting at the receptor channel complex) and competitive (acting at the NMDA recognition site) or modulatory sites (glycine, polyamine).

Although a competitive channel blocker can reduce damaging overstimulation of the excitatory portion of the receptor, it is also likely to eliminate the receptor's normal physiological functions. Thus, cognitive and memory brain functions are compromised and hence, most channel blockers cannot be administered safely to humans. In contrast, antagonists of receptor modulatory sites inhibit the toxic effects of high glutamate concentrations while sparing physiologic functions of glutamate. Thus, modulatory antagonists such as a glycine site antagonist, can be safely administered to

COMPOUNDS OF THE INVENTION

Compounds of the invention include felbamate, quinoxalinediones including the ACEA compounds (1011, 1021, 1031, 1328), pyridazinoindole, ACPC (1-aminocyclopropane carboxylic acid), 1,4 dihydroquinoxaline-2,3-diones, 4-hydroxy-2-quinalones, 4-amino-2-carboxytetrahydroquinolines and trans-4-hydroxypipecolic acid-4-sulfate.

In vivo NMDA Receptor Imaging

The subject invention provides a technique to image and thus quantitate the NMDA receptor complex in neurological diseases in vivo. By radioactively labeling a compound which binds the glycine receptor, e.g., felbamate, to produce $^{13}$N-felbamate or $^{11}$C-felbamate, and administering the labeled compound to a patient, the NMDA receptor can be visualized and quantified by, e.g., positron-emission tomography (PET) scanning. This technique permits one to diagnose asymptomatic, preclinical individuals with a neurological disease involving glutamate and the NMDA receptor. In addition it identifies and assesses clinical efficacy of treatment. Synthesis of $^{14}$C-felbamate for autoradiographic distribution in animal brain has been described. (Cornford, E. M., *Epilepsia*, 37(1):15–18, 1996).

In a study of post-mortem brain tissue from Huntington's disease, glycine-site binding of the NMDA receptor was decreased in the caudate nucleus (62%) and frontal cortex (20%) which reflects the ongoing disease process (Reynolds, G. P., *J. Neurol. Sci.*, 25(2):46–9, 1994).

Radio actively labeled felbamate quantitates the NMDA receptors in pre-clinical asymptomatic patients. Radio actively labeled felbamate can be utilized to diagnose disease states prior to their clinical expression, when neuronal cell death has already significantly occurred. In a variety of neurological diseases, symptoms do not occur until levels of NMDA receptor are greatly reduced. Diseases where this diagnostic technique is particularly useful include Parkinson's, Huntington's, Alzheimer's, Tourette's, adrenoleukodystrophy, CNS vasculitis, mitochondrial myopathies, HIV dementia, depression, ALS, movement disorders and Down's Syndrome.

THERAPEUTIC USES OF THE COMPOUNDS OF THE INVENTION

Felbamate and other antagonist at the glycine site of the NMDA receptor are useful in the treatment of multiple neurologic diseases in which at least glutamate is involved in the pathophysiology. ACEA compounds are administered at daily doses between 1–150 mg/kg, most advantageously between 20–40 mg/kg in each of the disorders discussed below.

Prevention of Neuronal Degeneration and Brain Atrophy in Epilepsy

Epilepsy, a disease which has been characterized as a paroxysmal, self-sustaining and self-limited cerebral dysrhythmia, genetic or acquired in origin and physiologic or organic in mechanism. Epilepsy is usually classified, by clinical and electro-encephalographic observations, into four general classes:

1) Grand mal
2) Petit mal
3) Psychomotor (complex partial)
4) Autonomic

Those afflicted with epilepsy have one or a combination of the above seizure types.

Prior to the present invention, all drugs used in the treatment of epilepsy function as prophylactics against the symptoms of epilepsy, i.e., the reduction and control of epileptic seizures, rather than being prophylactics against the sequela of seizures, i.e., brain atrophy, cognitive dysfunction.

Although it is generally recognized that approximately 50% of epileptic patients can be controlled with presently available anti-epileptic medications, there is a continuing long felt need for more selective and less toxic anti-epileptic drugs. The desiratum of the art has been to provide a non-toxic, non-sedative, long-acting and highly effective anti-epileptic drug.

Glycine site antagonists have been shown to act as anticonvulsant agents (Croucher, M. J., *Neurosci. Lett.*, 118:29–32, 1990, Croucher, M. J., *Brain Res.*, 543:91–96, 1991) although glycine antagonists with low intrinsic efficacy have proconvulsant activity (Wlaz, P., *Eur. J. Neurosci.*, 6(11):1710–1719, 1994).

In a study of etiology of complex partial seizures using microdialysis, elevated levels of glutmate occur prior to a complex partial seizure in humans (During, M. J., *Lancet*, 341:1607–1610, 1993). In addition, resting levels of glutamate were elevated in the temporal lobes of these patients. The elevated levels of glutamate in patients with complex partial seizures are suspected to be an etiology of brain atrophy (i.e., hippocampus) observed on brain MRI.

According to the subject invention, patients with complex seizures are administered a glycine site NMDA antagonist such as felbamate, even if other drugs are effective for seizure control, to prevent neuronal degeneration and brain atrophy ("neuroprotection"). The antagonist is administered to patients with seizure disorders to prevent future delayed cellular necrosis in the event that a seizure or status epilepticus occurs. The antagonist has a neuroprotective effect after status epilepticus, even when induced by mechanisms other than that of the NMDA receptor (Chronopoulis, A., *Epilepsia*, 34(2):359–366, 1993). Felbamate, administered chronically in oral doses of 100–15,000 mg/day, advantageously 1200–7200 mg/day (serum levels ranging from 25–300 µg/ml), is efficacious in attenuating neuronal cell death and atrophy in epilepsy.

Sepsis

In systemic blood infections, coma and cardiac/respiratory dysfunction can lead to death. Coma and neurological dysfunction occur after the administration of antibiotics, which are believed to increase the release of toxins as they kill bacteria. Elevated levels of quinolinic acid cause neuronal death by NMDA receptor overstimulation. Toxins from the bacteria are believed to increase the production of cytokines and CSF-quinolinic acid (Heyes, M., *Brain*, 116:1425–1450, 1993) causing neurological symptoms and neuronal cell death by NMDA receptor overstimulation. A glycine site NMDA antagonist such as felbamate attenuates neurological morbidity and mortality in sepsis. Felbamate can be administered most advantageously by the intravenous route or chronically in oral doses at the time of diagnosis. Felbamate, administered in oral doses of 100–15,000 mg/day, advantageously 1200–7200 mg/day (serum levels ranging from 25 µg–300 µg/ml), is efficacious in preventing neuronal cell death in sepsis.

Meningitis

Both viral and bacterial meningitis have been found to increase CSF-quinolinic acid levels (Heyes, M., *Brain*, 116:1425–1450, 1993). The neurological morbidity and mortality may be caused by excessive NMDA receptor stimulation. A glycine site NMDA antagonist prevents neurological morbidity and mortality in meningitis.

Felbamate can be administered most advantageously by the intravenous route or chronically in oral doses at the time of diagnosis of meningitis. Felbamate, administered in oral doses of 100–15,000 mg/day, advantageously 1200–7200 mg/day (serum levels ranging from 25 µg–300 µg/ml), is efficacious in preventing neuronal cell death in meningitis.

Adrenoleukodystrophy

Adrenoleukodystrophy (ADL) is an X-linked recessive disorder of myelin metabolism which causes seizures and dementia in young males. Pathologically, it has characteristics of an inflammatory disorder, suggesting that cytokines and quinolinic acid are involved in its etiology. A glycine site NMDA antagonist has efficacy as an anticonvulsant as well as a neuroprotectant.

Felbamate, administered chronically in oral doses of 100–15,000 mg/day, advantageously 1200–7200 mg/day (serum levels ranging from 25 µg–300 µg/ml), is efficacious in preventing neuronal death and seizures in ADL.

CNS Vasculitis

CNS vasculitis, an inflammatory condition of the cerebral arteries, occurs in multiple autoimmune diseases (i.e., rheumatoid arthritis). Neurological sequela include stroke, seizures and dementia. Quinolinic acid has been found to be elevated and correlate with the degree of brain damage by MRI and clinical dementia.

A glycine site NMDA antagonist has efficacy in preventing the neurological the sequela of CNS vasculitis (stroke, seizure and dementia). Felbamate, administered chronically in oral doses ranging from 100–15,000 mg/day, advantageously 1200–7200 mg/day (serum levels ranging from 25 µg–300 µg/ml), is efficacious in preventing neuronal degeneration in CNS vasculitis.

Impotence

Penile erection is induced by the NMDA receptor activation of nitric oxide in the paraventricular nucleus of the hypothalamus (Melis, M. R., Neuro. Sc. Lett., 179:9–12, 1994). Epilepsy patients treated with felbamate, an antagonist at the glycine site of the NMDA receptor complex, reported an increase in libido. A common side effect of felbamate is increased mental energy and alertness.

A glycine site NMDA antagonist decreases primary and secondary impotence. Felbamate, administered chronically in oral doses ranging from 100–15,000 mg/day, advantageously 1200–7200 mg/day (serum levels ranging from 25 µg–300 µg/ml), is efficacious in increasing sexual libido.

Schizophrenia

Schizophrenia is a chronic psychotic disorder which is believed to be caused by a dopamine metabolic disorder. Genetic influences are involved and brain atrophy occurs both in schizophrenic patients and in their asymptomatic monozygotic twins. A glutamate hypothesis with NMDA involvement has been suggested to be also involved in the pathophysiology of schizophrenia (Olney, J. W., Arch. Gen. Psych., 52:998–1007, 1995). D-cycloserine, a partial agonist at the glycine site of the NMDA receptor, caused deterioration of the patient's psychotic symptoms in schizophrenia (Cascella, N. G., J. Neurol. Transm. Gen. Sect., 95(2):105–111, 1994).

A selective interaction between glutamate and dopaminergic mechanisms involving NMDA receptors in the limbic forebrain has been suggested by the ability of glycine site antagonists to selectively antagonize the stimulant effects of d-amphatamine on dopamine synthesis in rat nucleus accumbens but not in striatum (Hutson, P. H., Br. J. Pharmacol., 103:2037–2044, 1991). Haldol, a common treatment for schizophrenia, has properties of a partial agonist for the strychnine-insensitive glycine site on the NMDA receptor (Fletcher, E. J., Eur. J. Pharmacol., 235 (2–3): 291–295, 1993).

Glycine site antagonists, including felbamate, function as "atypical neuroleptics" in the treatment of schizophrenia and other psychoses (Leeson, P. D., J. Med. Chem., 37(24):4053–4067, 1994). A glycine site NMDA antagonist such as felbamate, is a treatment for glutamate induced atrophy in patients with schizophrenia. Felbamate, administered chronically in oral doses ranging from 100–15,000 mg/day, advantageously 1200–7200 mg/day (serum levels ranging from 25 µg–300 µg/ml), is efficacious in preventing neuronal degeneration and brain atrophy in schizophrenia.

Drug Addiction

Symptoms of drug withdrawal in drug addiction may be in part mediated by the NMDA receptor complex. A glycine site antagonist at the NMDA receptor with properties of oral or IV administration, good tolerability, and low adverse experience profile is a treatment for drug addiction, tolerance, dependency and withdrawal. Felbamate, administered chronically in oral doses ranging from 100–15,000 mg/day, advantageously 1200–7200 mg/day (serum levels ranging from 25 µg–300 µg/ml), is efficacious in preventing the autonomic and mental adverse experiences of drug addiction.

Multiple Sclerosis

A portion of the cortical brain damage that occurs in acute attack of multiple sclerosis (MS) and chronic progressive MS is due to an inflammatory upregulation of cytokines and quinolinic acid. (Heyes, M., Brain, 116:1425–1450, 1993) Brain atrophy and cognitive dysfunction are common in MS.

A glycine site NMDA antagonist has efficacy in protecting cortical neurons ("neuroprotection") in MS. Felbamate, administered chronically in oral doses ranging from 100–15,000 mg/day, advantageously 1200–7200 mg/day (serum levels ranging from 25 µg–300 µg/ml), is efficacious in preventing neuronal degeneration in MS.

Fatigue

Fatigue is common in chronic diseases (i.e., multiple sclerosis, post-polio syndrome, Parkinson's) and in chronic fatigue syndrome. Chronic fatigue syndrome is believed to have a viral component in its etiology with involvement of cytokine up-regulation and potentially NMDA stimulation.

A glycine site NMDA antagonist provides symptomatic relief of fatigue as well as providing neuroprotection in the various disease states. Felbamate, administered chronically in oral doses ranging from 100–15,000 mg/day, advantageously 1200–7200 mg/day (serum levels ranging from 25 µg–300 µg/ml), is efficacious in treating fatigue of central nervous system etiology.

Lead Poisoning

Chronic or acute lead poisoning produces neuronal symptoms and brain damage by excessive stimulation of the NMDA receptor. Lead has been postulated to bind to the zinc binding site in the NMDA ion channel. Chronic treatment of rats with lead showed a slight increase in NMDA receptor density in the adult forebrain homogenates (Schulte, S., Neurotoxicology, 16(2):309–317, 1995).

A glycine site NMDA antagonist provides acute and prophylactic neuronal protection by controlling both NMDA function and quantity in these conditions. Felbamate, administered chronically in oral doses ranging from 100–15,000 mg/day, advantageously 1200–7200 mg/day (serum levels ranging from 25 µg–300 µg/ml), is efficacious in preventing neuronal degeneration from lead poisoning.

Mitochondrial Myopathies

Mitochondrial Myopathies are characterized by a mitochondrial abnormality (intracellular structures which produce energy for the cells) and other inherited or acquired biochemical disorders. Diseases or conditions include MELAS syndrome, MERF syndrome, Leber's disease, Wernicke's encephalopathy, Rett syndrome, homocystinuria, hyperprolinemia, nonketotic hyperglycinemia, hydroxybutyric aminoaciduria, sulfite oxidase deficiency, and combined systems disease (B12 deficiency).

A glycine site NMDA antagonist provides neuronal protection in these conditions. Felbamate, administered chronically in oral doses ranging from 100–15,000 µg/day, advantageously 1200–7200 mg/day (serum levels ranging from 25 µg–300 µg/ml), is efficacious preventing neuronal degeneration in mitochondrial myopathies.

HIV Dementia

Patients who become HIV(+) have early pre-clinical brain neuronal deterioration as measured by NMR spectroscopy.

When HIV(+) patients convert to AIDS, brain involvement produces dementia and is universally fatal. The mechanisms of brain deterioration appear to involve production of substances (i.e., quinolinic acid) that activate NMDA receptors and cause neuronal death by inducing intra cellular $Ca^{++}$ overload.

Blocking the NMDA receptor at the glycine site functions as neuroprotection and prevents neuronal death. Felbamate, administered chronically in oral doses ranging from 100–15,000 mg/day, advantageously 1200–7200 mg/day (serum levels ranging from 25 µg–300 µg/ml), is efficacious in preventing neuronal degeneration in HIV dementia.

Pain The centers of pain-transmitting structures in the spinal cord, thalamus and certain layers of the cerebral cortex contain NMDA receptors. Intractable tic douloureux (Chesire, W. P., Clin. J. Pain, 11:139–142, 1995), has been effectively treated with felbamate at doses of 1200–2400 mg/day. Conditions such as peripheral neuropathy, terminal cancer pain and failed back surgery which are intractable to current treatment modalities benefit from felbamate treatment. In the formalin injection animal pain model, glycine site antagonists (Millan, M. J., Neurosci. Lett., 178(1):139–143, 1994, Vaccarino, A. L., Brain Res., 615(2):331–334, 1993) decreased the late phase pain response. In a rat model of painful peripheral neuropathy, felbamate produced significant reductions in all measures of pain (Imamura, I., J. Pharm. Exp. The., 275(1):177–182, 1995). Specifically, the action of felbamate was antihyperalgesic and antiallodynic rather than analgesic.

Blocking the NMDA receptor at the glycine site prevents chronic pain transmission and gives symptomatic relief without producing central nervous system side effects. Felbamate, administered chronically in oral doses ranging from 100–15,000 mg/day, advantageously 1200–7200 mg/day (serum levels ranging from 25 µg–300 µg/ml), is efficacious in alleviating chronic pain.

Depression

Felbamate, a glycine site antagonist improves cognitive function and mood when administered to epileptic patients. Vegetative depression is characterized by low mood, excessive somnolence and obesity.

Vegetative depression responds to a glycine antagonist by increasing mood, having a stimulatory effect and producing weight loss by NMDA mechanisms. In addition, activation of the NMDA receptor, which are partly located on the serotinergic nerve terminal, elicits a release of cortical serotonin (Fink, K., Naumyn Schmiedebergs Arch. Pharmacol., 352(4):394–401, 1995) a major neurotransmitter in depression. Felbamate, administered chronically in oral doses ranging from 100–15,000 mg/day, advantageously 1200–7200 mg/day (serum levels ranging from 25 µg–300 µg/ml), is efficacious in treating vegetative depression.

Amyotrophic Lateral Sclerosis

Amyotrophic Lateral Sclerosis (ALS) is a progressive disease of the motor tracts of the brainstem and spinal cord which produces muscle weakness, wasting and death. Excessive glutmate stimulation may be involved in the pathogenesis of this disease (Rothstein, J. D., Ann. Neurol., 28:18–25, 1990). The number of NMDA receptors in the spinal cord is reduced in patients with ALS (Shaw, P. J., Brain Res., 637:297–302, 1994). Abnormal glycine and glutmate metabolism produce neurotoxicity by NMDA mechanisms (Virgo, L., Brain Res., 676:196–204, 1995).

A glycine site antagonist, which prevents these NMDA receptors from being excessively stimulated, prevents weakness and death in ALS. Felbamate, administered chronically in oral doses ranging from 100–15,000 mg/day, advantageously 1200–7200 mg/day (serum levels ranging from 25 µg–300 µg/ml), is efficacious in preventing ALS.

Parkinson's Disease

Parkinson's Disease (PD) is a selective degeneration of predominately $D_2$ dopaminergic neurons in the substantia nigra (motor portion of the basal ganglia) which produces progressive motor symptoms of rigidity and bradykinesia (slowness of movement). An NMDA-excitatory mechanism of early neuronal cell death is involved in the etiology of PD. Felbamate has been shown to antagonize the $D_2$ (dopamine receptor) in an animal model of cataplexy (Kretchmer, B. D., Neurosci Lett., 179(1–2):115–118, 1994).

An NMDA glycine site antagonist which prevents NMDA receptors form being excessively stimulated, prevents progressive motor weakness and death (neuroprotection) in PD. Felbamate, administered chronically in oral doses ranging from 100–15,000 µg/day, advantageously 1200–7200 mg/day (serum levels ranging from 25 µg–300 µg/ml), is efficacious in preventing neuronal death in PD.

Attention Deficit Disorder

Attention Deficit Disorder (ADD) is a brain disorder characterized impulsiveness, excessive motor symptoms and cognitive impairment. Current treatment includes the use of amphetamines which stimulate the brain. A glycine site NMDA antagonist has properties of cognitive enhancement and mental stimulation, without the side effects of dependency and decreased stature of amphetamines.

A glycine site NMDA antagonist is a useful treatment for ADD. Felbamate, administered chronically in oral doses ranging from 100–15,000 mg/day, advantageously 1200–7200 mg/day (serum levels ranging from 25 µg–300 µg/ml), is efficacious in treating ADD.

Narcolepsy

Narcolepsy is a sleep disorder in which patients have an acute onset of REM (dreaming) sleep. A glycine site NMDA antagonist has properties of cognitive enhancement and mental stimulation.

A glycine site NMDA antagonist is a useful treatment for narcolepsy. Felbamate, administered chronically in oral doses ranging from 100–15,000 mg/day, advantageously 1200–7200 mg/day (serum levels ranging from 25 µg–300 µg/ml), is efficacious in treating narcolepsy.

Alzheimer's Disease

Alzheimer's Disease (DAT) is a progressive dementing illness which is caused by an abnormal form of amyloid deposition in the brain. Excessive amyloid deposition induces glutamate toxicity of the NMDA receptor, resulting in neuronal death in areas of the brain that have a high density of NMDA receptors such as the hippocampus and cerebral cortex (areas of maximal neuronal death in DAT). The decrease in binding of NMDA receptors in DAT visual cortex correlated with increased numbers of neurofibrillary tangles. (Carlson, M. D., Neurobiol. Aging, 14(4): 343–352, 1993). Studies in animals have shown that glycine antagonist improve learning and attenuate scopalamine memory deficits (Fishkin, R. J., Behav. Neurol. Biol., 59(2):150–157, 1993, Finkelstein, J. E., Pharmacol. Biochem. Behav., 49(3):707–710, 1994, Baxter, M. G., Neurobiol. Aging, 15(2):207–213, 1994).

A glycine site NMDA antagonist with cognitive enhancement and neuronal protection properties is a useful treatment for DAT. Felbamate, administered chronically in oral doses ranging from 100–15,000 mg/day, advantageously 1200–7200 mg/day (serum levels ranging from 25 µg–300 µg/ml), is efficacious in preventing neuronal degeneration in DAT.

Childbirth

All childbirth deliveries carry a risk of complications including premature labor, prolonged labor, hypoxia, etc. which place the fetus at risk for cerebral ischemic damage and cerebral palsy.

A glycine site NMDA antagonist with properties of excellent placental permeability, no teratogenesis and non-toxic properties to the fetus is a valuable prophylactic treatment to all mothers in labor. Felbamate is administered most advantageously intravenously or orally within 24 hours of expected delivery. Felbamate, administered chronically in oral doses ranging from 100–15,000 mg/day, advantageously 1200–7200 mg/day (serum levels ranging from 25 µg–300 µg/ml), is efficacious in preventing neuronal damage in childbirth delivery.

Surgical Anesthesia

All patients who undergo general anesthesia for any surgical procedure are at risk for hypoxia, anoxia, cerebral embolism (i.e., fat, air), hypotension, hypoglycemia etc. which place the brain at risk for permanent damage.

A glycine site NMDA antagonist with neuronal protection properties is a useful prophylactic treatment in all anesthetized patients. Felbamate can be administered most advantageously intravenously or orally within 4–24 hours of surgery. Felbamate, administered chronically in oral doses ranging from 100–15,000 mg/day, advantageously 1200–7200 mg/day (serum levels ranging from 25 µg–300 µg/ml), is efficacious in preventing neuronal damage during surgical anesthesia.

Traumatic Head and Spinal Cord Injury

In the rat SDH (acute subdural hemaroma) model, both pre and post treatment with a glycine site antagonist significantly reduced hemispheric ischemic damage (Tsuchida, E., *J. Neurotrauma*, 12(3):279–288, 1995). Patients with head and spinal cord injury have been found to have elevated cerebrospinal fluid levels of quinolinic acid which implicates the NMDA receptor in the etiology of neuronal cell death.

A glycine site NMDA antagonist with neuronal protection properties is a useful prophylactic treatment in all head and spinal cord injured patients by protecting against hypoxia and glutamate stimulation of the NMDA receptor. Felbamate can be administered most advantageously intravenously or orally within minutes of the diagnosis of traumatic brain or spinal cord injury. Felbamate, administered chronically in oral doses ranging from 100–15,000 mg/day, advantageously 1200–7200 mg/day (serum levels ranging from 25 µg–300 g/ml), is efficacious in preventing neuronal death in brain or spinal cord injury.

Hypoglycemia

Patients who suffer from an acute lowering of the blood sugar are at risk for cerebral brain damage by mechanisms involving the AMPA and NMDA receptor.

A glycine site NMDA antagonist with neuronal protection properties is a useful prophylactic or acute treatment of hypoglycemia. Felbamate can be administered most advantageously intravenously or orally within minutes of the diagnosis of hypoglycemia. Felbamate, administered chronically in oral doses ranging from 100–15,000 mg/day, advantageously 1200–7200 mg/day (serum levels ranging from 25 µg–300 g/ml), is efficacious in preventing neuronal death in hypoglycemia.

Tourette's Syndrome

Tourette's syndrome is disorder of the basal ganglia which results in spontaneous movements and vocalizations. Damage to the basal ganglia may be due to glutamate or glutamate-like toxins mediated via the NMDA receptor.

A glycine site NMDA antagonist with neuronal protection properties is a useful treatment of Tourette's syndrome. Felbamate, administered chronically in oral doses ranging from 100–15,000 µg/day, advantageously 1200–7200 mg/day (serum levels ranging from 25 µg–300 µg/ml), is efficacious in preventing neuronal death in Tourette's Syndrome.

Hepatic Encephalopathy

Hepatic encephalopathy is characterized by severe liver disease producing secondary neurological symptoms including seizures, cognitive dysfunction and extrapyramidal movements. NMDA receptors are involved in producing the latter three symptoms.

A glycine site NMDA antagonist with neuronal protection properties is a useful prophylactic treatment in all hepatic failure patients. Felbamate, administered chronically in oral doses ranging from 100–15,000 mg/day, advantageously 1200–7200 mg/day (serum levels ranging from 25 µg–300 µg/ml), is efficacious in preventing neuronal death in treating seizures and neuronal degeneration in hepatic encephalopathy.

Movement Disorders

NMDA receptors are located in the subcortical areas of the brain which are involved in motor control. In a mouse model of posthypoxic myoclonus (a condition of hyperexcitability of the central nervous system), felbamate was found to have antimyoelonie properties. Felbamate has shown efficacy in control of tremor (Edwards, K. R., *Neurology*, 45:1951, 1995) and hemifacial spasm (Mellick, G. A., *J. Pain and Symptom Management*, 10:392–395, 1995) in humans at doses between 1800–2800 mg/day.

A glycine site antagonist is useful in the treatment of all movement disorders. Felbamate, administered chronically in oral doses ranging from 100–15,000 mg/day, advantageously 1200–7200 mg/day (serum levels ranging from 25 µg–300 µg/ml), is efficacious in preventing neuronal death in treating movement disorders and preventing neuronal degeneration in movement disorders.

Cognitive Enhancement in Normal Senescence

Glutamate activation of the NMDA receptor has been postulated to be involved in the process of neuronal plasticity and long term memory (Monaghan, D. T., *Annu. Rev. Pharmacol. Toxicol.*, 29:365–402, 1989). Age-related decreases in strychnine-insensitive glycine binding which may be associated with impairments of learning and memory which occur in aging animals (Miyoshi, R., *Synapse*, 6:338–343, 1990).

A glycine site NMDA antagonist, such as felbamate, administered chronically in oral doses ranging from 100–15,000 mg/day, advantageously 1200–7200 mg/day (serum levels ranging from 25 µg–300 µg/ml), is efficacious in preventing a decrease in cognitive function with normal aging.

Down's Syndrome (Trisomy 21)

Down's syndrome is a chromosomal syndrome with a frequency of 1 in 700 births. Mild retardation is universal and Alzheimer's disease, with neurofibrillary tangles and neuritic plaques, develop after the 40th year of life.

A glycine site NMDA antagonist such as felbamate, increases cognitive capabilities and can prevent the onset of Alzheimer's disease in Down's syndrome. Felbamate, administered chronically in oral doses ranging from 100–15,000 mg/day, advantageously 1200–7200 mg/day (serum levels ranging from 25 µg–300 µg/ml), is efficacious in preventing neuronal degeneration in Down's Syndrome.

Electroshock Therapy (ECT)

Patients who undergo ECT may suffer cognitive complications including memory loss. Since ECT is an artificially induced seizure, neuronal damage is similar to that of chronic seizures. A mechanism of cognitive dysfunction is damage to the NMDA receptors of the hippocampus and cerebral cortex. ECT has been shown to increase the turnover of NMDA receptors in animals.

A glycine antagonist such as felbamate prevents NMDA induced neuronal damage from ECT treatment. Felbamate is administered most advantageously intravenously or orally prior to the administration of ECT. Felbamate, administered chronically in oral doses ranging from 100–15,000 mg/day, advantageously 1200–7200 mg/day (serum levels ranging from 25 µg–300 µg/ml), is efficacious in preventing neuronal damage and delayed cellular necrosis as a consequence of ECT therapy.

Brain Tumors Brain tumors produce elevated levels of quinolinic acid (Heyes, M., *J. Neurol. Sci.*, 133:112–118-, 1995) which produce seizures, neuronal degeneration and brain atrophy.

A glycine site antagonist such as felbamate, administered chronically in oral doses of 100–15,000 mg/day, advantageously 1200–7200 mg/day (serum levels ranging from 25 µg–300 µg/ml), is efficacious in preventing seizures, neuronal degeneration and brain atrophy from brain tumors.

Cerebellar Degeneration

Cerebellar NMDA receptors have a different pattern of modulation at glutamate and glycine sites compared to the forebrain. Thus, glycine plays a more critical role in the control of cerebellar NMDA function (Widdowson, P. S., *J. Neurochem.*, 64(2):651–61, 1995). Atrophy is common in cerebellar degeneration.

A glycine site antagonist such as felbamate, administered chronically in oral doses of 100–15,000 mg/day, advantageously 1200–7200 mg/day (serum levels ranging from 25 µg–300 µg/ml), is efficacious in preventing cerebellar degeneration.

Having now fully described this invention it will be appreciated by those skilled in the art that the same can be performed within a wide range of equivalent parameters of composition, conditions, and modes of administration without departing from the spirit or scope of the invention or any embodiment thereof.

What is claimed is:

1. A method of treating sepsis and preventing neuronal degeneration and cell death in a human having sepsis, the method comprising the steps of:
   administering to the human having sepsis a neuronal cell protecting antagonist of the glycine site of the NMDA receptor complex, wherein said antagonist is 2-phenyl-1,3-propandeiol dicarbamate at a serum level ranging from 25–300 µg/ml, in order to significantly attenuate neurological morbidity by preventing excessive stimulation of the NDMA receptor.

2. A method of treating HIV dementia and preventing neuronal degeneration comprising the steps of:
   administering to a human having HIV dementia a neuronal cell protecting antagonist of the glycine site of the NDMA receptor complex, said antagonist being 2-phenyl-1,3-propandeiol dicarbamate at a serum level ranging from 25–300 µg/ml, in order to attenuate neurological morbidity by preventing excessive stimulation of the NMDA receptor in the human having HIV dementia.

3. A method of treating meningitis comprising the steps of:
   chronically administering to a human having meningitis a neuronal cell antagonist of the glycine site of the NMDA receptor complex, wherein said antagonist is felbamate at a serum level ranging from about 25–300 µg/ml.

4. A method of treating CNS vasculitis and preventing neuronal degeneration and cell death in a human having CNS vasculities, the method comprising the steps of:
   administering to the human having CNS vasculitis neuronal cell protecting antagonist of the glycine site of the NMDA receptor complex, wherein said antagonist is 2-phenyl-1,3-propandeiol dicarbamate at a serum level ranging from 25–300 µg/ml, in order to significantly attenuate neurological morbidity by preventing excessive stimulation of the NDMA receptor.

5. A method as in claim 1 wherein said felbamate is administered intravenously.

6. A method as in claim 1 wherein said felbamate is administered orally or rectally.

* * * * *